(12) United States Patent
Sra

(10) Patent No.: US 6,926,714 B1
(45) Date of Patent: Aug. 9, 2005

(54) METHOD FOR PULMONARY VEIN ISOLATION AND CATHETER ABLATION OF OTHER STRUCTURES IN THE LEFT ATRIUM IN ATRIAL FIBRILLATION

(76) Inventor: Jasbir S. Sra, W305 N2963 Red Oak Ct., Pewaukee, WI (US) 53072

( * ) Notice: Subject to any disclaimer, the term of this patent is extended or adjusted under 35 U.S.C. 154(b) by 91 days.

(21) Appl. No.: 10/353,625

(22) Filed: Jan. 29, 2003

Related U.S. Application Data

(60) Provisional application No. 60/354,561, filed on Feb. 5, 2002.

(51) Int. Cl.[7] ............................................. A61B 18/18
(52) U.S. Cl. ....................................... 606/41; 607/122
(58) Field of Search ............................. 606/41, 45–50; 607/101, 102, 115, 122; 604/95.04; 128/898

(56) References Cited

U.S. PATENT DOCUMENTS

| | | |
|---|---|---|
| 4,547,892 A | 10/1985 | Richey et al. |
| 4,660,571 A | 4/1987 | Hess et al. |
| 4,807,621 A | 2/1989 | Hagen et al. |
| 4,940,064 A | 7/1990 | Desai |
| 5,245,282 A | 9/1993 | Mugler, III et al. |
| 5,255,679 A | 10/1993 | Imran |
| 5,341,807 A | 8/1994 | Nardella |
| 5,575,766 A | 11/1996 | Swartz et al. |
| 5,575,772 A | 11/1996 | Lennox |
| 5,611,777 A | 3/1997 | Bowden et al. |
| 5,642,736 A | 7/1997 | Avitall |
| 5,676,662 A | 10/1997 | Fleischhacker et al. |
| 5,687,723 A * | 11/1997 | Avitall .......................... 600/374 |
| 5,702,438 A | 12/1997 | Avitall |
| 5,720,775 A | 2/1998 | Larnard |
| 5,730,704 A | 3/1998 | Avitall |
| 5,807,249 A | 9/1998 | Qin et al. |
| 5,910,129 A * | 6/1999 | Koblish et al. .......... 604/95.03 |
| 5,931,811 A | 8/1999 | Haissaguerre et al. |
| 6,086,581 A | 7/2000 | Reynolds et al. |
| 6,179,809 B1 * | 1/2001 | Khairkhahan et al. ... 604/95.04 |
| 6,266,553 B1 | 7/2001 | Fluhrer et al. |
| 6,383,151 B1 | 5/2002 | Diederich et al. |
| 6,485,455 B1 | 11/2002 | Thompson et al. |
| 6,502,576 B1 | 1/2003 | Lesh |
| 6,503,247 B2 | 1/2003 | Swartz et al. |
| 6,527,769 B2 | 3/2003 | Langberg et al. |

(Continued)

OTHER PUBLICATIONS

Feinberg WM, et al. Prevalence, age distribution and gender of patients with atrial fibrillation, ArchIntern Med 1995;155: 469-473.

(Continued)

*Primary Examiner*—Michael Peffley
(74) *Attorney, Agent, or Firm*—Jansson, Shupe & Munger, Ltd.

(57) ABSTRACT

A catheter design for ablating AF based upon the true anatomy of the left atrium and especially the left atrial pulmonary vein junction, obtained by unique imaging techniques. The catheter design will conform to the true anatomy of the anatomical structures to be ablated and takes into account the complex 3-D geometry of the left atrium and the various sizes and shapes of the pulmonary veins and their openings into the left atrium.

15 Claims, 7 Drawing Sheets

U.S. PATENT DOCUMENTS

| | | | |
|---|---|---|---|
| 6,542,781 B1 * | 4/2003 | Koblish et al. | 607/122 |
| 6,546,270 B1 | 4/2003 | Goldin et al. | |
| 6,549,606 B1 | 4/2003 | Vaillant et al. | |
| 6,556,695 B1 | 4/2003 | Packer et al. | |
| 6,572,612 B2 | 6/2003 | Stewart et al. | |
| 6,610,058 B2 | 8/2003 | Flores | |
| 6,616,655 B1 | 9/2003 | Falwell et al. | |
| 6,628,743 B1 | 9/2003 | Drummond et al. | |
| 6,629,987 B1 | 10/2003 | Gambale et al. | |
| 6,632,223 B1 | 10/2003 | Keane | |
| 6,702,811 B2 * | 3/2004 | Stewart et al. | 606/41 |
| 6,811,544 B2 * | 11/2004 | Schaer | 604/95.04 |
| 2004/0225331 A1 * | 11/2004 | Okerlund et al. | 607/14 |

OTHER PUBLICATIONS

Haissaguerre M, et al. Spontaneous initiation of atrial fibrillation by ectopic beats originating in the pulmonary veins. N Engl J Med 1998;339:659-666.

Cox, JL, et al. Electrophysiology, Pacing and Arrhythmias, "Operation for Atrial Fibrillation". Clin Cardiol 1991;4: 827-834.

Fuster V, et al. ACC/AHA/ESC guidelines for management of patients with atrial fibrillation: A report of the American College of Cardiology/American Heart Association Task Force on Practice Guidelines and Policy Conference. J AM Coll Cardiol 2001;38:1266.

Sra J, et al. Atrial fibrillation: Epidemiology, mechanisms and management. Curr Probl Cardiol 2000;25(7):405-524.

Pappone C, et al. Mortality, morbidity, and quality-of-life after circumferential pulmonary vein ablation for atrial fibrillation: Outcomes from a controlled, nonrandomized long-term study. J AM Coll Cardiol 2003;42:185-197.

"Catheter Ablation to Treat AF", Atrial Fibrillation Foundation web site printout, 2002.

"Surgical Treatment for Atrial Fibrillation", The University of Chicago Hospitals web site printout, admitted prior art.

"Radiofrequency Pulmonary Vein Isolation in Patients with Atrial Fibrillation", Michael Argenziano, MD, Director, Columbia Surgical Arrhythmia Program web site printout, admitted prior art.

* cited by examiner

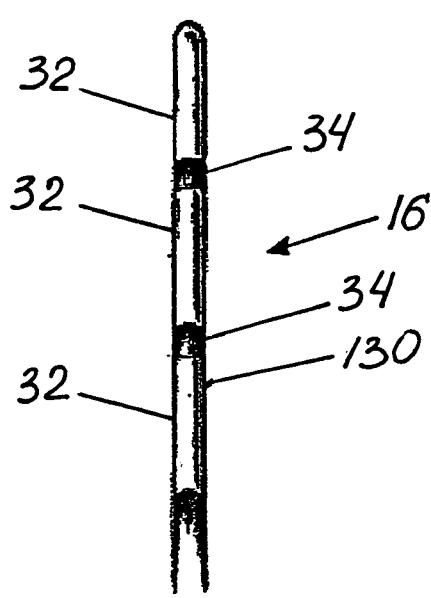
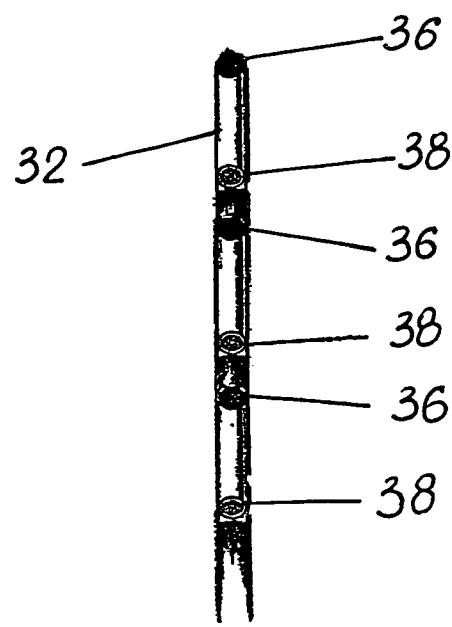
FIG. 6A    FIG. 6B
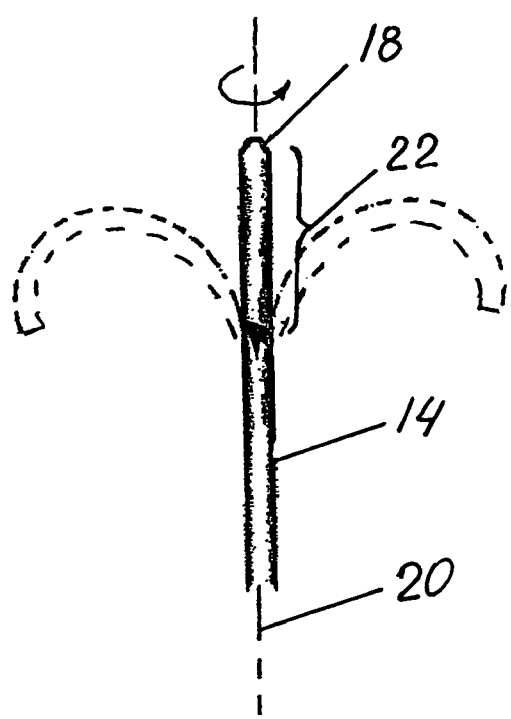
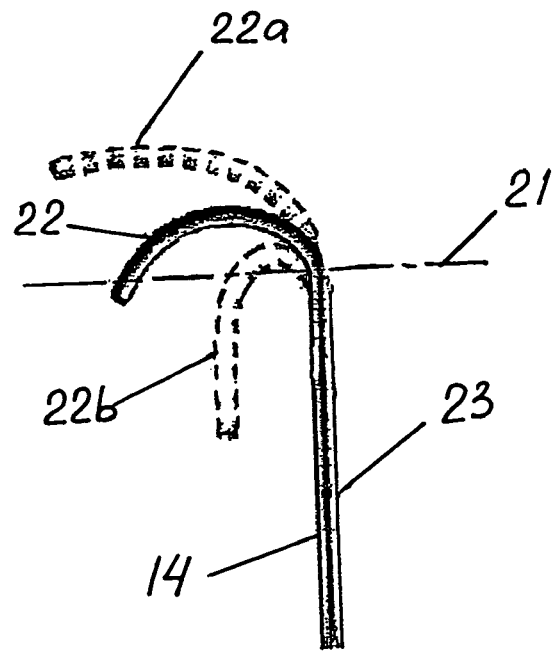
FIG. 4A    FIG. 4B

METHOD FOR PULMONARY VEIN ISOLATION AND CATHETER ABLATION OF OTHER STRUCTURES IN THE LEFT ATRIUM IN ATRIAL FIBRILLATION

CROSS REFERENCE TO RELATED APPLICATION

The present invention is based on and claims priority to U.S. Provisional Patent Application Ser. No. 60/354,561 filed on Feb. 5, 2002.

FIELD OF THE INVENTION

The present invention generally relates to a catheter design which can be used to treat atrial fibrillation (AF). More specifically, the present invention relates to a catheter design that can be used to electrically isolate pulmonary veins from the left atrium and conform to the true anatomy of the pulmonary veins based on images obtained using computed tomographic (CT) imaging techniques.

BACKGROUND OF THE INVENTION

A short discussion of atrial fibrillation, or AF, and its mechanisms is useful in understanding the complexity of the problem and how the method and apparatus of the present invention will help treat this arrhythmia more effectively.

Atrial fibrillation, which is an arrhythmia in which the atria (upper chambers of the heart) stop contracting as they fibrillate, is the most common of the heart rhythm problems. Present data suggests that AF is the most common arrhythmia-related cause of hospital admissions. Patients with AF have a high incidence of medically significant complications such as stroke and congestive heart failure. Premature atrial contractions can act as triggers and initiate paroxysms of AF. These premature atrial contractions have been shown to predominantly originate in the pulmonary veins from the left atrium. Since infrequent and nonreproduceable premature atrial contractions limit the utility of ablating trigger sites, a variety of surgical and catheter techniques have been used to isolate the pulmonary veins from the left atrium.

One of the surgical techniques used to treat AF involves the use of radio-frequency waves (modified electrical energy) to create small scars on the heart's surface near the connection between the pulmonary veins and the left atrium. The small scars created by the radio-frequency waves stop the erratic impulses of atrial fibrillation by directing the impulses to follow a normal electrical pathway through the heart. Typically, this type of surgical procedure is performed through a chest incision. Surgeons use specially designed instruments to deliver radio-frequency waves to the abnormal tissue, typically during open heart surgery performed for other reasons, such as a mitral valve repair. Although this type of surgical technique is effective when the patient is undergoing open heart surgery for another reason, catheter-related treatment methods are more practical when the patient does not require the invasive open heart surgery for other reasons.

One of the catheter techniques involves the application of radio-frequency energy at areas showing double potentials suggestive of sites capable of conducting between the left atrium and the pulmonary veins. The currently crude three-dimensional reconstruction of the left atrium, the inability of the physician to visualize the pulmonary vein ostia from inside, the varying size of the pulmonary veins and thus the pulmonary vein ostia, the difficulty in keeping the mapping catheter stable at the pulmonary vein ostia sites, all make current approaches to mapping using fluoroscopically-guided imaging techniques cumbersome, lengthy and inadequate.

Because of these limitations, radio-frequency ablation is much less successful than surgery, especially in patients with persistent atrial fibrillation. In fact, less than 20 percent of patients undergoing radio-frequency catheter ablation for AF benefit from this approach.

A number of modalities presently exist for medical diagnostic imaging. One such approach utilizes computed tomographic imaging to delineate the precise anatomy of an organ. Once the left atrium and pulmonary veins are visualized, a catheter design which will conform to the anatomy of the different pulmonary veins will help isolate the pulmonary veins more precisely and easily and assure the same success rate for the radio-frequency approach as for surgery.

SUMMARY OF THE INVENTION

One aspect of the present invention is a catheter designed to be used in planning cardiac interventional procedures to treat AF. The catheter design is based upon the precise anatomy of the left atrium obtained using a medical imaging system, such as CT imaging, for left atrial mapping.

In accordance with the present invention, three-dimensional images of the left atrium and endocardial or navigator (inside views) of the left atrium are used as a guide to design a catheter that will conform to the anatomical structures which figure prominently in the treatment of AF and other heart rhythm problems. The catheter design of the present invention is utilized with a 3-D image of the left atrium created by using predetermined protocols. Endocardial (inside) or navigator views of the left atrium will then be obtained and stored on a transferable medium. The acquired database will be transferred to the computer workstation of the interventional system and registered with the interventional system over which the mapping and ablation catheter is visualized.

Using a transseptal catheterization, which is a standard technique for gaining access to the left atrium, the catheter of the present invention is introduced into the left atrium. The catheter consists of a main catheter shaft and a tip section that is capable of bidirectional steerability. The distance from the transition point from the catheter shaft to the outer tip of the tip section may vary to accommodate different atrial sizes. The catheter shaft length may also vary depending upon the height of the patient and the size of the left atrium.

The catheter of the present invention includes a recording and ablation catheter embedded in the main catheter shaft. The recording and ablation catheter includes an electrode section having three 5 mm electrodes. The electrode section of the ablation and recording catheter comes out of the catheter shaft in a circular fashion, such that one, two or all three electrodes may be out of the shaft. As the electrode section of the recording and ablation catheter is moved further and further out of the shaft, the pre-stressed curve of the electrode section causes the catheter to move in a circular fashion around the pulmonary vein ostium. Intracardiac recordings and real-time visualizations of the catheter determine which electrodes can be used for ablation. One, two, or all three electrodes can be used simultaneously for ablation.

The design of the steering handle of the catheter includes actuator controls that ensure a proper curve of the catheter shaft and the degree of protrusion of the catheter from the catheter shaft. The catheter steering handle further includes locking mechanisms to lock the catheter shaft and catheter in place.

Further aspects of the invention are disclosed herein. The above presentation and its advantages and the various features of the concept of this invention will be appreciated further from the drawings and the detailed descriptions which follow.

BRIEF DESCRIPTION OF THE DRAWINGS

The drawings illustrate the best mode presently contemplated of carrying out the present invention.

In the drawings:

FIGS. 4a–4b are a side view of the catheter shaft of the present invention and illustrating the movement of the catheter shaft in a bidirectional plane;

FIGS. 6a–6b are a detailed view of the mapping and ablation catheter of the present invention illustrating three mapping and ablation electrodes;

DETAILED DESCRIPTION OF THE INVENTION

Figure 1:
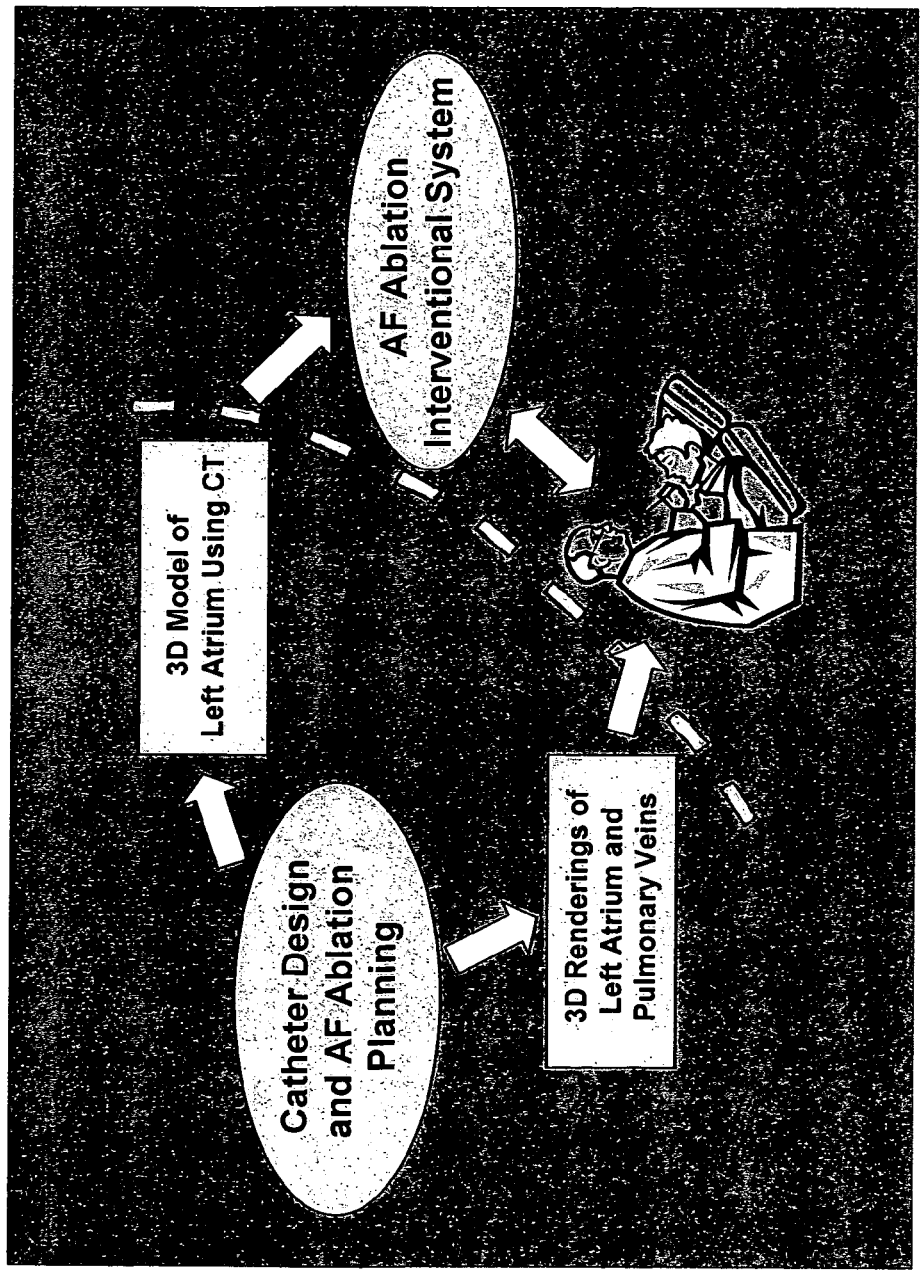
FIG. 1 is a conceptual illustration of the method of the present invention to use a specifically designed catheter for the ablation of atrial fibrillation, including the 3-D modeling of the left atrium and pulmonary veins using a CT image.

Referring first to FIG. 1, thereshown is a diagram illustrating the overview of an exemplary process in which a cardiac CT scan is performed to create a 3-D image of the left atrium of a patient's heart. Once the 3-D image of the left atrium is acquired, the image can be used for interventional planning for such things as atrial fibrillation (AF) ablation. The volume of patient data acquired using the CT imaging is optimized for the left atrium and cardiac gating is performed to acquire consecutive axial images from the same phase of the cardiac cycle. Once the CT imaging has been completed, a 3-D reconstruction of the left atrium is created.

Figure 2:
FIG. 2 is a three-dimensional CT image of the left atrium and pulmonary veins.

Once the 3-D reconstruction of the left atrium is created, a segmentation process is used to extract the inner surface of the left atrium, as illustrated in FIG. 2. As shown in FIG. 2, the topographic contours of the left atrium can be readily viewed, as well as the ostium between two pulmonary veins and the left atrium. The 3-D and inner views of the left atrium are stored into a file and transferred to a computer workstation of the interventional system. Once the information is transferred to the computer workstation, the information is registered and viewed by an interventionalist.

The cardial CT imaging in accordance with the present invention provides information for AF interventional planning (i.e. an accurate rather than a crude 3-D geometric representation of the left atrial-pulmonary vein junction and other structures). The increased accuracy of the geometry of these structures, in combination with a catheter designed in accordance with the present invention, allows the interventionalist to identify and quickly ablate the relevant structure.

The present invention is directed to a catheter design that conforms to the anatomy of the left atrial-pulmonary vein junctions and other important structures such as the left atrial appendage and the left atrial wall between the right and left pulmonary veins. The catheter design of the present invention eliminates the flaws in current techniques used in AF ablation. Presently available catheter designs do not conform to the anatomy of the left atrial-pulmonary vein junction. Additionally, this junction is difficult to precisely identify using current fluoroscopic and echocardiographic techniques.

Figure 3:
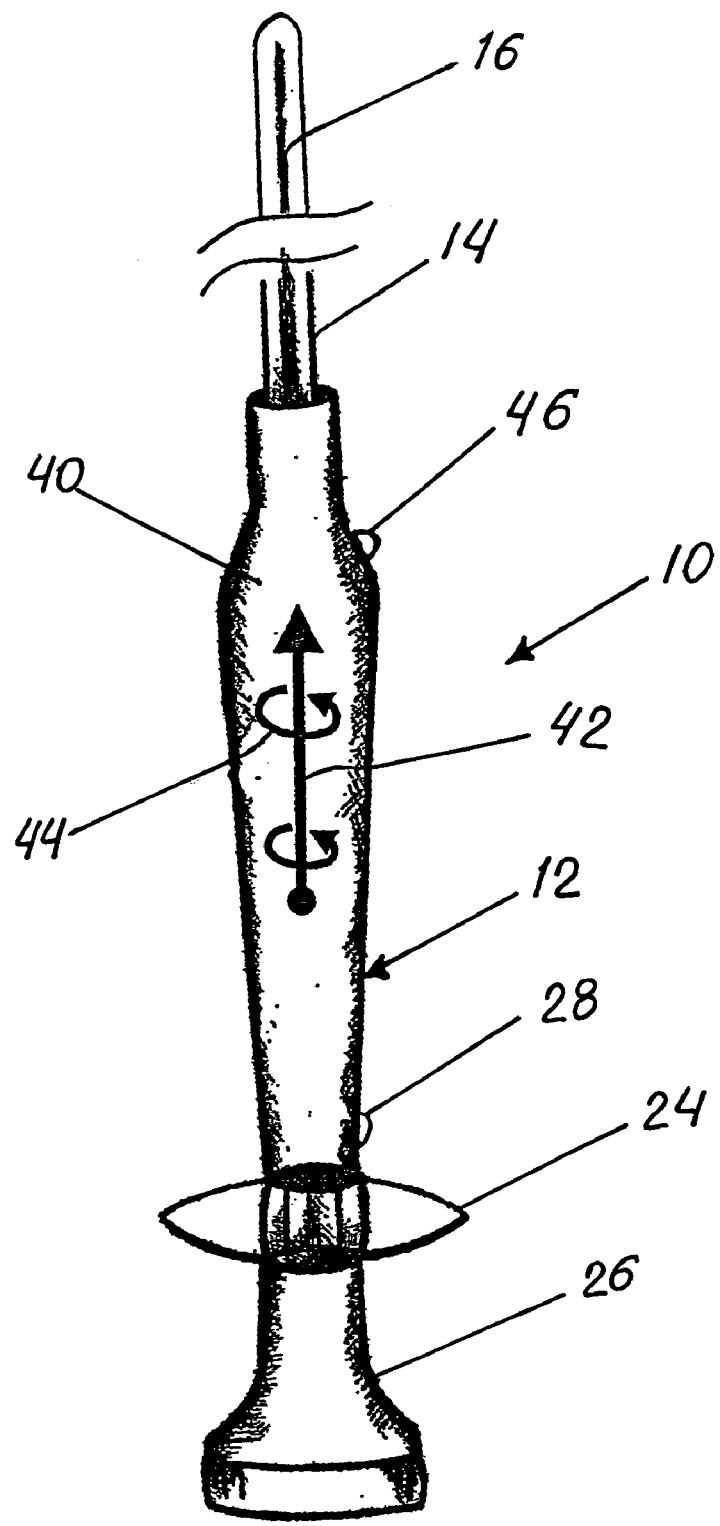
FIG. 3 is a view of the steering handle for the catheter shaft and mapping and ablation catheter of the present invention.

Referring now to FIG. 3, thereshown is a catheter 10 of the present invention. The catheter 10 includes a steering handle 12, a catheter shaft 14 and an internal mapping and ablation catheter 16. The internal wiring and controls for the catheter, and specifically the ablation catheter 16, are not shown but will be described in detail below. The catheter shaft 14 extends from the steering handle 12 and encloses the mapping and ablation catheter 16. The catheter shaft 14 provides support for the mapping and ablation catheter 16 as the catheter shaft is inserted into the patient using a standard technique for gaining access to the patient's left atrium, such as transseptal catheterization. It is contemplated by the inventor that at least three different catheter shaft lengths can be available depending upon the height of the patient and the size of the left atrium.

Referring now to FIGS. 4a and 4b, the catheter shaft 14 extends to an outer tip 18. In the preferred embodiment of the invention, the outer tip 18 of the catheter shaft 14 is radio-opaque such that it can be visualized in real-time over the x-ray fluoroscopy.

As illustrated in FIG. 4a, the catheter shaft 14 extends along a central axis 20. As illustrated in FIG. 4a, the tip section 22 is rotatable about the central axis 20, as illustrated by the broken lines in FIG. 4a. The rotation of the tip section 22 about the center axis 20 allows the interventionalist to control the orientation of the catheter when inserted into the left atrium, as will be described below.

Referring back to FIG. 3, an upper actuator 24 is included on the catheter handle 12 for controlling the rotation of the catheter shaft tip section 22 about central the axis 20 illustrated in FIG. 4a. Thus, the operator can control the rotation of the tip section 22 by rotating the upper actuator 24.

As illustrated in FIG. 4b, the tip section 22 of the catheter shaft 14 can be moved up to a 60° angle above the original bidirectional base plane 21 that passes through the transition between the main body 23 and the tip section 22, as shown by reference numeral 22a. Further, the tip section 22 is capable of a 300° angle curve downward relative to the base plane 21, as illustrated by the dashed lines and reference character 22b. The rotation of the catheter shaft 14 about the center axis 20, as well as the angled movement of the tip section 22 relative to a bidirectional plane 21, allows the catheter shaft to be moved both posteriorly or anteriorly from the original plane as desired.

In the embodiment of the invention illustrated, the tip section 22 may vary from 1.5 inches to 3 inches depending upon the size of the patient in which the catheter of the present invention is being used. The bidirectionality of the catheter shaft, the different curve sizes, and the ability to bend the catheter up to a 300° angle downward and 60° upward from the bidirectional plane allows the shaft to be oriented towards the appropriate pulmonary vein once inserted into the left atrium.

Referring back to FIG. 3, a lower actuator 26 on the steering handle 12 controls the angled movement of the tip section 22, as illustrated in FIG. 4b. Specifically, rotation of the actuator 26 in a clockwise direction results in movement of the catheter up to a 300° angled curve to the position shown by reference numeral 22b. If the lower actuator 26 is rotated in a counter-clockwise direction from a neutral location, the catheter tip section 22 is movable up to a 60° angle from the original bidirectional base plane 21, as shown by reference numeral 22a. Thus, rotation of the lower actuator 26, in connection with the rotation of the upper actuator 24, allows for the desired orientation of the tip section 22.

Referring back to FIG. 3, the steering handle 12 includes a locking mechanism 28 for the movement of the catheter shaft 14. The locking mechanism 28 secures the catheter shaft in a desired curve or position once the proper orientation of the catheter shaft has been achieved through movement of the upper actuator 28 and the lower actuator 26.

As described previously, the catheter 10 of the present invention includes an internal mapping and ablation catheter 16 within the catheter shaft 14. Referring now to FIG. 6, thereshown is a detailed view of the mapping and ablation catheter 16 of the present invention. As illustrated in FIG. 6, the mapping and ablation catheter 16 includes an electrode section 30 that includes three electrodes 32. The electrodes 32 are spaced from each other by spacer sections 34. In the preferred embodiment of the invention, each of the electrodes is approximately 5 mm in length while the interelectrode spacing is approximately 2 mm.

In the preferred embodiment of the invention, each of the electrodes 32 is configured to ablate heart muscle. The ablation can be carried out using various types of energy sources, such as microwave, laser, cryothermy, ultrasound and conventional radio-frequency signals. Each of the electrodes 32 is independently operable such that either one, two or three of the electrodes can be used to ablate heart tissue during a procedure performed using the catheter 16 of the present invention.

Referring now to FIG. 6b, each of the electrodes 32 includes a temperature recording site 36 and a bipolar electrocardiogram recording site 38. The temperature recording site 36 allows the temperature to be recorded from the tip of each electrode 32 while the bipolar electrocardiogram recording site 38 allows an electrocardiogram to be determined in a bipolar fashion.

Figures 5A, 5B:
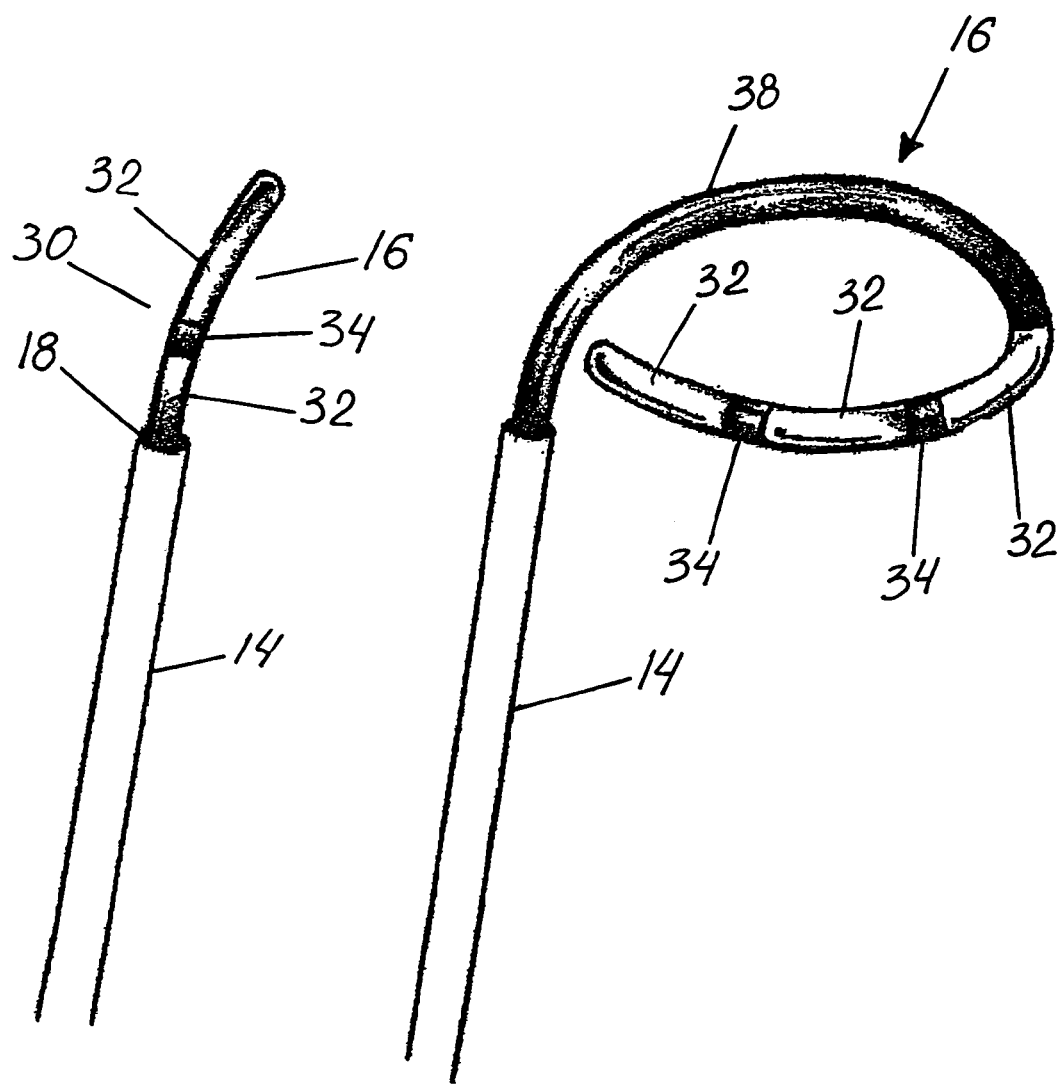
FIGS. 5a–5b are a side view illustrating the mapping and ablation catheter of the present invention as it is deployed from the catheter shaft.

Referring now to FIGS. 5a and 5b, thereshown is the movement of the electrode section 30 of the mapping and ablation catheter 16 out of the catheter shaft 14. As illustrated in FIG. 5a, only the first electrode 32 extends past the tip 18 of the catheter shaft 14. As the mapping and ablation catheter 16 is moved out of the catheter shaft 14, the catheter 16 comes out in a circular fashion as shown in FIG. 5b. The circular shape of the electrode section 30 is controlled by the pre-stressed curve of the electrode section 30. The curvature of the electrode section 30 allows the electrode section 30 to move along the curved inner wall of the pulmonary vein. Depending upon the electrode or electrodes in contact with the atrial tissue, one, two or all three electrodes can be used to ablate the heart tissue.

When fully deployed, the proximal and distal ends of the catheter 16 are adjacent to each other as illustrated in FIG. 5b. Additionally, the catheter 16 is at a right angle to the catheter shaft 14 such that the electrode section 30 can be used to ablate a ring around the junction between the pulmonary vein and the atrial wall. As illustrated in FIG. 5b, a non-recording and ablating section 38 of the mapping and ablation catheter 16 provides for the required curvature of the mapping and ablation catheter 16. The non-recording section 38 does not include any electrodes and thus does not function in the recording or ablation process.

Referring back to FIG. 3, the steering handle 12 includes an upper actuator 40 that is used to control the movement of the mapping and ablation catheter 16 into and out of the catheter shaft 14. The upper actuator 40 is moveable both in a longitudinal direction, as illustrated by arrow 42, and is rotatable about a longitudinal axis, as illustrated by arrow 44. When the upper actuator 40 is moved in the direction illustrated by arrow 42, the mapping and ablation catheter 16 is slowly extended from the catheter shaft 14, as illustrated in FIG. 5a. When the upper actuator 40 is rotated as illustrated by arrow 44, the curvature of the ablation catheter 16 is adjusted. It is contemplated that three separate curves of 10 mm, 15 mm and 20 mm can be created by rotating the upper actuator 40. The different curvatures of the ablation catheter 16 allows the ablation catheter to be adjusted for different patient sizes and thus different pulmonary vein dimensions.

Once the mapping and ablation catheter 16 has been extended the required distance and achieved the desired curvature, an upper locking mechanism 46 can be actuated to lock the mapping and ablation catheter 16 into a desired configuration.

Figure 7:
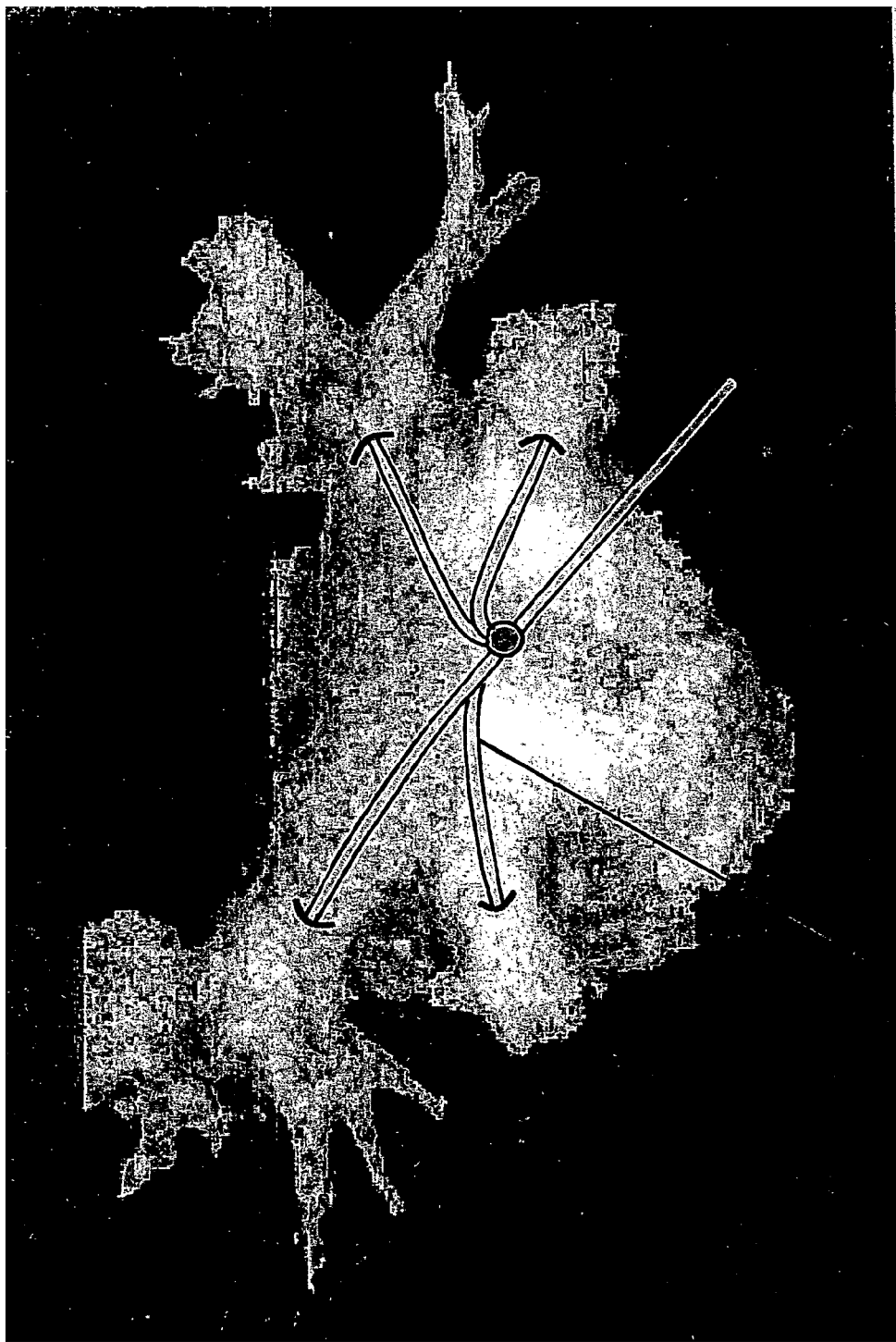
FIG. 7 is a view of the deployment of the catheter shaft in the left atrium as imposed over a three-dimensional CT image.
Figure 8A:
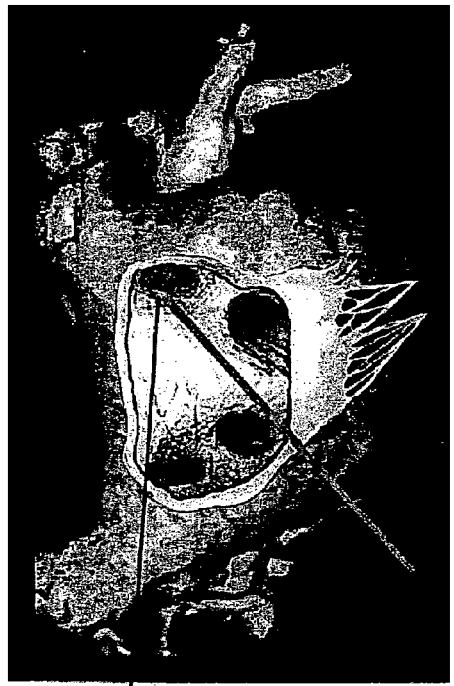
FIGS. 8A-8D is a sequential illustration of the movement of the mapping and ablation catheter in a sequential fashion around the pulmonary vein ostium with the front end of the left atrium open to illustrate the pulmonary vein ostia and their orientation to the left atrium.
Figure 8B:
Figure 8C:
Figure 8D:

Referring now to FIG. 7, thereshown is the introduction of the catheter shaft of the present invention into the left atrium using the transseptal approach. FIG. 7 shows the posterior view of the left atrium with the right pulmonary veins on the right side and the left pulmonary veins on the left side. As illustrated, the catheter shaft 14 can be bent at different curve angles and orientations depending upon the pulmonary vein that needs to be accessed. Once the catheter shaft has been bent to the desired orientation, the mapping and ablation catheter 16 can be extended from the outer tip of the catheter shaft to ablate the desired areas.

Referring now to FIG. 8, thereshown is the introduction of the catheter shaft 14 and the extension of the mapping and ablation catheter 16 therefrom to ablate a ring around the junction of the pulmonary vein and the atrium wall. As illustrated in FIG. 8d, once the ablation catheter 16 has been fully extended, the desired areas have been ablated as illustrated by the dark ring 50 of FIG. 8.

While the invention has been described with reference to the left atrium and AF, it is understood that it could be utilized for other rhythm problems and other chambers. Other imaging techniques such as magnetic resonance imaging or x-ray fluoroscopy, could be used in place of CT.

Similarly, although the concepts of the invention introduced above are discussed with respect to cardiac imaging and ablation, it is understood that the method of acquisition of data and ablation is not limited to cardiac and medical applications but may be utilized in non-cardiac applications such as ablation in other organs and structures. Also, the methodology described may be utilized in non-medical applications. Delivered energy may be understood to mean radio-frequency current, microwave energy, cryo or other forms of energy.

In addition, while the invention has been described with reference to its exemplary embodiments, it will be understood by those skilled in the art that various changes may be made without departing from the scope of the invention. In addition, changes and modifications may be made in order to adapt to a particular situation or material without departing from the essential scope thereof. Therefore, it is intended that the invention not be limited to the particular embodiment disclosed as the best method for carrying out this invention, but that the invention will include all embodiments falling within the scope of the appended claims.

Various alternatives and embodiments are contemplated as being within the scope of the following claims particularly pointing out and distinctly claiming the subject matter regarded as the invention.

I claim:

1. A method of catheter ablation and pulmonary vein isolation in the left atrium to treat atrial fibrillation, the method comprising the steps of:
    obtaining a three-dimensional rendering of the left atrium and pulmonary veins utilizing cardiac image data;
    providing a catheter apparatus operable to ablate selected cardiac tissue upon contact therewith, the catheter apparatus comprising:
        a hollow catheter shaft having a main body extending along a central axis and a tip section joined to the main body, the catheter shaft being rotatable about the central axis and the tip section being movable above and below a base plane extending through a transition point between the main body and the tip section, the base plane being generally perpendicular to the central axis;
        an ablation catheter positioned in the catheter shaft, the ablation catheter having an electrode section selectively movable into and out of the tip section of the catheter shaft, the electrode section of the ablation catheter having a plurality of electrodes each operable to ablate a selected area of tissue in contact with the electrode; and
        a steering handle coupled to both the catheter shaft and the ablation catheter for controlling the rotation of the catheter shaft about the central axis, the movement of the catheter shaft about the base plane and the extension of the ablation catheter out of the catheter shaft;
    tracking the movement of the catheter apparatus on the three-dimensional rendering of the left atrium and pulmonary veins as the catheter is inserted into the heart until the catheter apparatus is in a desired location;
    extending the electrode section of the ablation catheter from the catheter shaft such that the electrode section is positioned in contact with the pulmonary vein to be ablated; and
    actuating the electrodes on the electrode section of the ablation catheter to ablate desired locations on the pulmonary vein.

2. The method of claim 1 wherein the step of actuating the electrodes on the electrode section includes selectively activating the electrodes as the electrode section of the ablation catheter is extended from the catheter shaft.

3. The method of claim 1 wherein each of the electrodes on the electrode section of the ablation catheter is independently operable.

4. The method of claim 1 wherein the electrode section of the ablation catheter has a pre-stressed curve such that as the electrode section extends out of the catheter shaft, the electrode section assumes the pre-stressed curve.

5. The method of claim 1 wherein the step of tracking the movement of the catheter apparatus on the three-dimensional rendering includes providing a stored three-dimensional rendering of the left atrium and tracking the movement of the catheter apparatus in near real-time.

6. The method of claim 1 further comprising the steps of:
    moving the tip section of the catheter shaft to a desired orientation;
    rotating the catheter shaft to a desired position such that the catheter shaft is positioned adjacent to the portion of the pulmonary vein to be ablated; and
    extending the electrode section from the catheter shaft such that the electrode section assumes a pre-stressed curve that is perpendicular to the central axis of the catheter shaft.

7. The method of claim 1 wherein the steering handle includes a first actuator operable to rotate the catheter shaft about the central axis.

8. The method of claim 7 wherein the steering handle includes a second actuator operable to move the tip section of the catheter shaft above and below the base plane.

9. The method of claim 8 wherein the steering handle includes a third actuator operable to extend and retract the electrode section of the ablation catheter from the catheter shaft.

10. The method of claim 3 wherein the ablation catheter includes three electrodes, each separated by non-ablation sections.

11. The method of claim 3 wherein each of the electrodes includes both a temperature recording site and an electrocardiogram recording site.

12. The method of claim 4 wherein the pre-stressed curve of the electrode section is perpendicular to the central axis of the catheter shaft.

13. The method of claim 7 wherein the diameter of the curve is adjustable.

14. The method of claim 1 wherein the cardiac image data is acquired using medical diagnostic imaging.

15. The method of claim 14 wherein the medical diagnostic imaging is computed tomographic (CT) imaging.

* * * * *